United States Patent
Shindo et al.

(10) Patent No.: US 12,083,424 B2
(45) Date of Patent: *Sep. 10, 2024

(54) GAMIFICATION OF HEALTH AWARENESS BASED ON SLEEP PATTERNS

(71) Applicant: The Pokemon Company, Tokyo (JP)

(72) Inventors: Takayuki Shindo, Tokyo (JP); Satoshi Ogawa, Tokyo (JP); Kaname Kosugi, Tokyo (JP); Marie Shuto, Tokyo (JP); Koya Nakahata, Tokyo (JP)

(73) Assignee: THE POKEMON COMPANY, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/878,045

(22) Filed: Aug. 1, 2022

(65) Prior Publication Data
US 2022/0362665 A1 Nov. 17, 2022

Related U.S. Application Data

(63) Continuation of application No. 17/206,193, filed on Mar. 19, 2021, now Pat. No. 11,433,303, which is a
(Continued)

(30) Foreign Application Priority Data

Sep. 21, 2018 (JP) .................. 2018-176957

(51) Int. Cl.
*A63F 13/42* (2014.01)
*A61B 5/00* (2006.01)
(Continued)

(52) U.S. Cl.
CPC .............. *A63F 13/42* (2014.09); *A63F 13/65* (2014.09); *A63F 13/69* (2014.09); *A63F 13/825* (2014.09);
(Continued)

(58) Field of Classification Search
CPC .......... A63F 13/42; A63F 13/65; A63F 13/69; A63F 13/825; A61B 5/4812
See application file for complete search history.

(56) References Cited

U.S. PATENT DOCUMENTS 10,401,799 B2  9/2019 Kusuda et al.
11,013,985 B2  5/2021 Nishimura
(Continued)

FOREIGN PATENT DOCUMENTS

JP  H11-164966 A  6/1999
JP  2016-002109 A  1/2016
(Continued)

OTHER PUBLICATIONS

International Search Report and Written Opinion mailed on Dec. 10, 2019, received for PCT Application PCT/JP2019/036820, Filed on Sep. 19, 2019, 10 pages.
(Continued)

*Primary Examiner* — William H McCulloch, Jr.
*Assistant Examiner* — Ankit B Doshi
(74) *Attorney, Agent, or Firm* — XSENSUS LLP

(57) ABSTRACT

A user breeds a virtual life form by practicing good sleep habits and stays motivated toward practicing good sleep habits while enjoying breeding the virtual life form. A game server manages progress of a breeding game of a virtual life form, the game server including circuitry configured to acquire sleep data that at least includes a sleep pattern indicating a bedtime and a wake-up time of a user; store the acquired sleep data as a sleep history; and update the breeding game based on the sleep pattern in the sleep history.

20 Claims, 14 Drawing Sheets

Related U.S. Application Data continuation of application No. PCT/JP2019/036820, filed on Sep. 19, 2019.

(51) Int. Cl.
  *A63F 13/65* (2014.01)
  *A63F 13/69* (2014.01)
  *A63F 13/825* (2014.01)

(52) U.S. Cl.
  CPC ........... *A61B 5/4812* (2013.01); *A61B 5/4815* (2013.01); *A61B 2503/12* (2013.01)

(56) References Cited

U.S. PATENT DOCUMENTS

| | | |
|---|---|---|
| 2016/0086500 A1 | 3/2016 | Kaleal, III |
| 2017/0136348 A1* | 5/2017 | Hattori .................. G16H 10/20 |

FOREIGN PATENT DOCUMENTS

| | | |
|---|---|---|
| JP | 2016-49237 A | 4/2016 |
| JP | 2016-198389 A | 12/2016 |
| JP | 2019-111182 A | 7/2019 |
| KR | 2017-0047430 A | 5/2017 |
| WO | 2016/021235 A1 | 2/2016 |

OTHER PUBLICATIONS

Japanese Office Action dated Sep. 7, 2022, issued in corresponding Japanese Patent Application No. 2021-112184.
Office Action issued on Jan. 11, 2023, in corresponding Japanese patent Application No. 2021-112184, 7 pages.
Office Action issued on Oct. 11, 2023, in corresponding Japanese patent Application No. 2023-079863 , 5 pages.

* cited by examiner

GAMIFICATION OF HEALTH AWARENESS BASED ON SLEEP PATTERNS

CROSS-REFERENCE TO RELATED APPLICATIONS

This application is a continuation of U.S. application Ser. No. 17/206,193, filed Mar. 19, 2021, which is a Bypass Continuation of National Stage Application based on PCT/JP2019/036820, filed on Sep. 19, 2019, which claims priority to Japanese Patent Application No. 2018-176957, filed on Sep. 21, 2018, the entire contents of each are incorporated herein by its reference.

TECHNICAL FIELD

The present disclosure relates to a game server, a program, a method, a game system, and an information processing terminal.

BACKGROUND

In recent years, activity measurement devices that measure actions and an amount of activity of a person using a motion detection sensor or the like that detects motions of a body have become widely used. An activity measurement device is designed to improve health awareness of a user by presenting the user with an amount of activity or the like and is desirably used on a continuous basis. For example, PTL 1 discloses an invention that heightens a user's awareness toward health in the process of enjoying a breeding game of a virtual life form based on measured biological data.

[PTL 1] Japanese Patent Application Publication No. 2007-117639

SUMMARY

Technical Problem

However, the description in PTL 1 merely reflects a parameter based on automatically-acquired biological data on the game and can hardly motivate a user to make it a habit of leading a well-regulated lifestyle in a continuous manner.

The present disclosure has been made in consideration of the problem described above and an object thereof is to provide a game server, a program, a method, a game system, and an information processing terminal for managing progress of a breeding game which enables a user to breed a virtual life form by leading a well-regulated lifestyle and, particularly, by practicing good sleep habits and which enables the user to stay motivated toward practicing good sleep habits while enjoying breeding the virtual life form.

Solution to Problem

In order to achieve the object described above, a game server according to the present disclosure is a server that manages progress of a breeding game of a virtual life form, the game server including: an acquiring unit which acquires sleep data that at least includes a sleep pattern indicating a bedtime and a wake-up time of a user; a sleep history storage unit which stores the acquired sleep data as a sleep history; and a processing unit which executes processing steps related to the breeding game based on the sleep pattern in the sleep history.

In addition, in order to achieve the object described above, a program according to the present disclosure is a program that manages progress of a breeding game of a virtual life form, the program causing a computer to function as: an acquiring unit which acquires sleep data that at least includes a sleep pattern indicating a bedtime and a wake-up time of a user; a sleep history storage unit which stores the acquired sleep data as a sleep history; and a processing unit which executes processing steps related to the breeding game based on the sleep pattern in the sleep history.

Furthermore, in order to achieve the object described above, a method according to the present disclosure is a method of managing progress of a breeding game of a virtual life form, the method including the steps of: acquiring sleep data that at least includes a sleep pattern indicating a bedtime and a wake-up time of a user; storing the acquired sleep data as a sleep history; and executing processing related to the breeding game based on the sleep pattern in the sleep history.

In addition, in order to achieve the object described above, a game system according to the present disclosure is a system in which a game server that manages progress of a breeding game of a virtual life form and a user terminal are connected to each other via a network, wherein the game server includes: an acquiring unit which acquires sleep data that at least includes a sleep pattern indicating a bedtime and a wake-up time of a user; a sleep history storage unit which stores the acquired sleep data as a sleep history; and a processing unit which executes processing steps related to the breeding game based on the sleep pattern in the sleep history.

Furthermore, in order to achieve the object described above, an information processing terminal according to the present disclosure is an information processing terminal that executes a breeding game of a virtual life form, the information processing terminal including: an acquiring unit which acquires sleep data that at least includes a sleep pattern indicating a bedtime and a wake-up time of a user; a sleep history storage unit which stores the acquired sleep data as a sleep history; and a processing unit which executes processing steps related to the breeding game based on the sleep pattern in the sleep history.

According to the present disclosure, since a user practicing a well-regulated lifestyle leads to the user breeding a virtual life form, the user can stay motivated toward practicing good sleep habits while enjoying breeding the virtual life form.

DETAILED DESCRIPTION

Hereinafter, embodiments of the present disclosure will be described with reference to the drawings. In all of the diagrams for explaining the embodiments, common components will be denoted by same reference signs and repetitive descriptions will be omitted. It is to be understood that the following embodiments do not unduly restrict the contents of the present disclosure as set forth in the scope of claims. In addition, not all components described in the embodiments are essential components of the present disclosure.

First Embodiment

Figure 1:
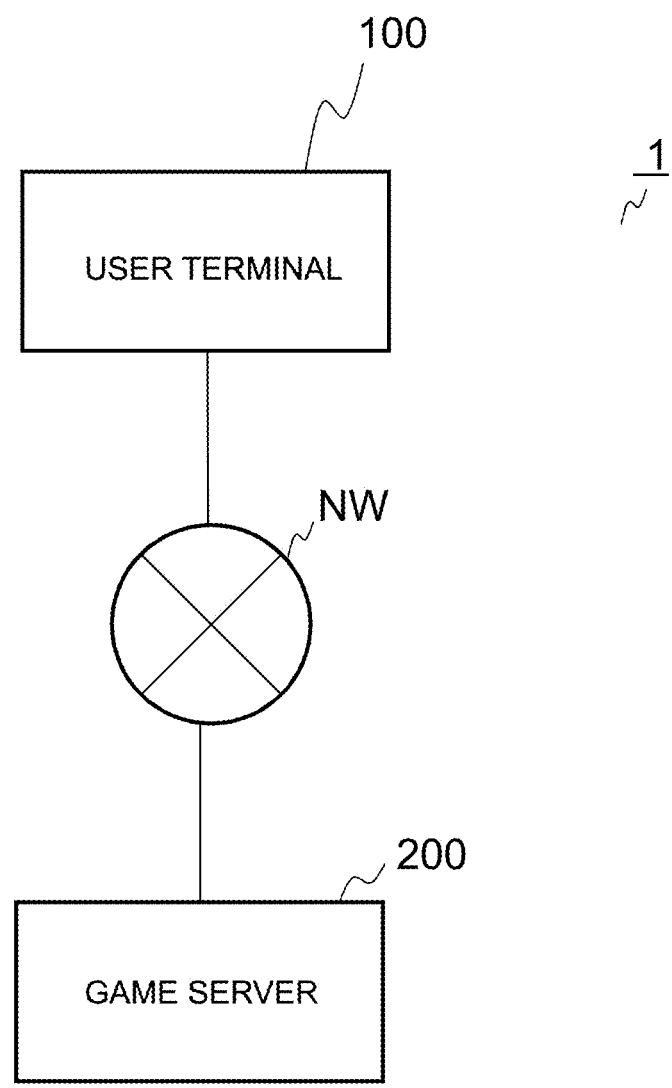
FIG. 1 is a configuration diagram of a game system 1.

FIG. 1 is a configuration diagram of a game system 1. A configuration of the game system 1 according to the first embodiment will be described with reference to FIG. 1.

The game system 1 includes a user terminal 100 and a game server 200 which are connected to be capable of communicating with each other via a network NW. The network NW is constituted by a WAN (Wide Area Network), a LAN (Local Area Network), or the like.

While only one user terminal 100 is shown in FIG. 1, in the present embodiment, the game system 1 includes a plurality of user terminals 100 of which each is provided for each user. The game system according to the present embodiment enables the user to stay motivated toward practicing good sleep habits in the process of enjoying a breeding game of a virtual life form.

The user terminal 100 detects sleep data of the user and transmits the sleep data to the game server 200. The sleep data at least includes a sleep pattern indicating a bedtime and a wake-up time of the user. In this case, a bedtime represents a time of day at which the user goes to sleep and may be, for example, a time of day at which the user goes to bed or a time of day at which the user's consciousness makes a transition from an awakened state to a state of sleep. In addition, a wake-up time represents a time of day at which the user awakes and may be, for example, a time of day at which the user gets out of bed or a time of day at which the user's consciousness makes a transition from a state of sleep to an awakened state. In the present embodiment, a pair of a bedtime and a wake-up time from going to sleep to waking up is referred to as a sleep pattern.

The game server 200 is a game server that manages progress of a breeding game of a virtual life form and provides a game service of breeding a virtual life form in accordance with a request from the user terminal 100. For example, the game server 200 delivers a game program to the user terminal 100 having accessed the game server 200 via the network NW and the game program is executed on the user terminal 100. The user terminal 100 having executed the game program transmits sleep data of the user to the game server 200.

The game server 200 acquires the sleep data from the user terminal 100 and stores the sleep data as a sleep history. In addition, the game server 200 executes processing steps related to the breeding game based on a sleep pattern based on the sleep history and a sleep pattern of the acquired sleep data, and transmits information related to the progress of the breeding game to the user terminal 100.

As described above, in the present embodiment, the user terminal 100 detects sleep data of the user and transmits the sleep data to the game server 200. In addition, the game server 200 executes processing steps related to the breeding game based on the sleep data and transmits a processing result to the user terminal 100. In other words, the user can stay motivated toward practicing good sleep habits while enjoying a breeding game that uses sleep data of the user as game input.

Figure 2:
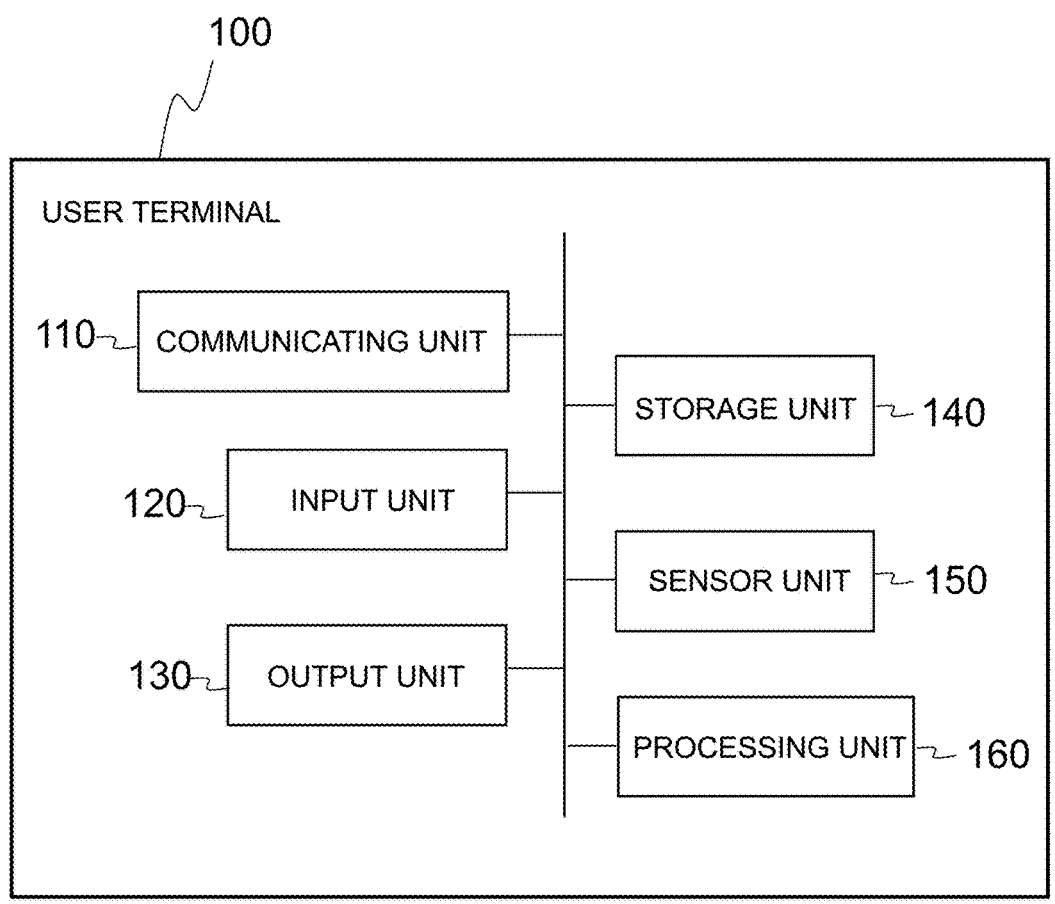
FIG. 2 is a functional block diagram showing an example of a functional configuration of a user terminal 100.

FIG. 2 is a functional block diagram showing an example of a functional configuration of the user terminal 100. Alternatively, the user terminal 100 according to the present embodiment may be configured by omitting a part of components (respective units) shown in FIG. 2.

The user terminal 100 is an information processing apparatus and, in the present embodiment, the user terminal 100 is, for example, a smartphone, a feature phone, a tablet computer, a laptop computer, a desktop computer, a portable game machine, a stationary game machine, a wearable terminal such as a head-mounted display, or a multifunctional device such as a multifunctional television receiver (a smart television) equipped with an information processing function.

In other words, the user terminal 100 has various functions (for example, an input function, an output (display) function, an information processing function, a network communication function, a sensor function, a call function, and a camera function) which are included in a general multifunctional device.

The network communication function is a function that enables communication via the Internet or the like and/or a function that enables communication via a mobile communication network. The user terminal 100 may be realized by installing a predetermined function in an existing multifunctional device. In the present embodiment, in addition to being used as the multifunctional device described above, the user terminal 100 is used to detect the sleep data described above and to execute the breeding game described above.

The user terminal 100 includes a communicating unit 110, an input unit 120, an output unit 130, a storage unit 140, a sensor unit 150, and a processing unit 160.

The communicating unit 110 performs various kinds of control for communicating with the game server 200 via the network NW and a function thereof can be realized by hardware such as various kinds of processors or a communication ASIC or by a program or the like.

The input unit 120 is an interface for accepting an input from the user and sends the user's input to the processing unit 160. For example, the input unit 120 can be one or more of a touch panel, a button, a microphone, and a controller. Alternatively, sensing data having been detected by the sensor unit 150 to be described later may be used as an input by the user. The user can perform an input related to the breeding game via the input unit 120.

The output unit 130 is, for example, a display apparatus such as a display and/or an audio output apparatus such as a speaker, and displays and/or outputs various kinds of images or audio generated by the user terminal 100 in accordance with an input with respect to the input unit 120 or displays or outputs various kinds of images or audio based on data received from the game server 200. The output unit 130 includes an artificial intelligence-mounted speaker (a smart speaker).

In addition, the output unit 130 may include an announcement function for prompting the user to wake up using a sound (such as an alarm), light, vibration, or the like. For example, when a reference wake-up time (described in detail with reference to FIG. 6) arrives or the reference wake-up time approaches, the output unit 130 may output a call or a motion (vibration) of the virtual life form or output light suggestive of the virtual life form. Alternatively, the output unit 130 may output a call of a virtual life form that differs from the virtual life form being bred by the user or music related to an item or the like so as to build up expectations of the user toward the progress of the game. Accordingly, the user can be motivated to wake up in the morning.

The storage unit 140 is a storage apparatus for storing a program and various kinds of data that cause a computer to function. The storage unit 140 may include a temporary storage area or a storage.

The sensor unit 150 represents various kinds of devices that detect various states of the user terminal 100. For example, the sensor unit 150 can be one or more of an altitude sensor (an acceleration sensor or a gyroscope sensor) that detects an altitude or an inclination of the terminal itself, an eye-gaze sensor that detects a direction of a line of sight of the user, a photosensor that detects peripheral brightness, and an infrared sensor that detects a motion of the user. Alternatively, or additionally, the sensor unit 150 may be one or more of a microphone that collects sound in the periphery of the user terminal 100, a humidity sensor that detects humidity in the periphery of the user terminal 100, a geomagnetic sensor that detects a magnetic field at a location where the user terminal 100 resides, and the like.

The sensor unit 150 may be configured to detect various kinds of information using the sensor functions described above. For example, the sensor unit 150 may detect the number of steps walked by the user who owns the user terminal 100 using the function of the acceleration sensor. Using the function of the acceleration sensor, the sensor unit 150 may detect motion information indicating whether the user terminal 100 is in motion or stationary or the like at regular intervals or every time the user terminal 100 is operated. The sensor unit 150 sends the sensing data detected as described above to the processing unit 160.

The sensor unit 150 is an information processing terminal (a so-called wearable terminal) which can be mounted to the user and which is connected to the user terminal 100 so as to be capable of communicating with the user terminal 100 such as a wrist watch-type terminal or a ring-type terminal. The sensor unit 150 may detect biological data of the user. For example, the sensor unit 150 determines a heart rate of the user by photoplethysmography or the like and sends the heart rate to the processing unit 160 as sensing data. The sensing data detected by the sensor unit 150 is not limited to the above and the sensor unit 150 may detect biological data related to the user's sleep such as breathing, pulse, or body motion.

The processing unit 160 executes various kinds of information processing to be executed in the user terminal 100. The processing unit 160 has a CPU (Central Processing Unit) and a memory. In the user terminal 100, the various kinds of information processing described above are executed by having the CPU use the memory to execute an information processing program stored in the storage unit 140. In the present embodiment, as the information processing described above, the processing unit 160 executes a processing step of calculating sleep data, a processing step of presenting the user with information related to the progress of the breeding game having been received from the game server 200, and the like. In addition, when the user terminal 100 operates as a multifunctional device, the processing unit 160 executes information processing for realizing the respective functions. Furthermore, the processing unit 160 acquires a present time and date using a system clock.

Based on the sensing data having been sent from the sensor unit 150, the processing unit 160 calculates a sleep pattern indicating a bedtime and a wake-up time of the user. In addition, the processing unit 160 instructs the communicating unit 110 to transmit the sleep pattern to the game server 200 as sleep data. It should be noted that the sleep pattern may be calculated using a function for analyzing sleep that is included in a general multifunctional device such as that described above, or the manner in which a bedtime and a wake-up time are calculated may be configured by a developer of the breeding game or the like. For example, a time at which the user performs an operation to put the virtual life form to sleep in the breeding game may be set as the bedtime and a time at which the user performs an operation to awake the virtual life form in the breeding game may be set as the wake-up time. As the operation to awake the virtual life form, for example, the virtual life form being displayed on a display may be tapped or the terminal may be shaken. Alternatively, a configuration may be adopted in which the processing unit 160 sends the sensing data having been sent from the sensor unit 150 to the game server 200 via the communicating unit 110 and the game server 200 calculates a sleep pattern.

Figure 3:
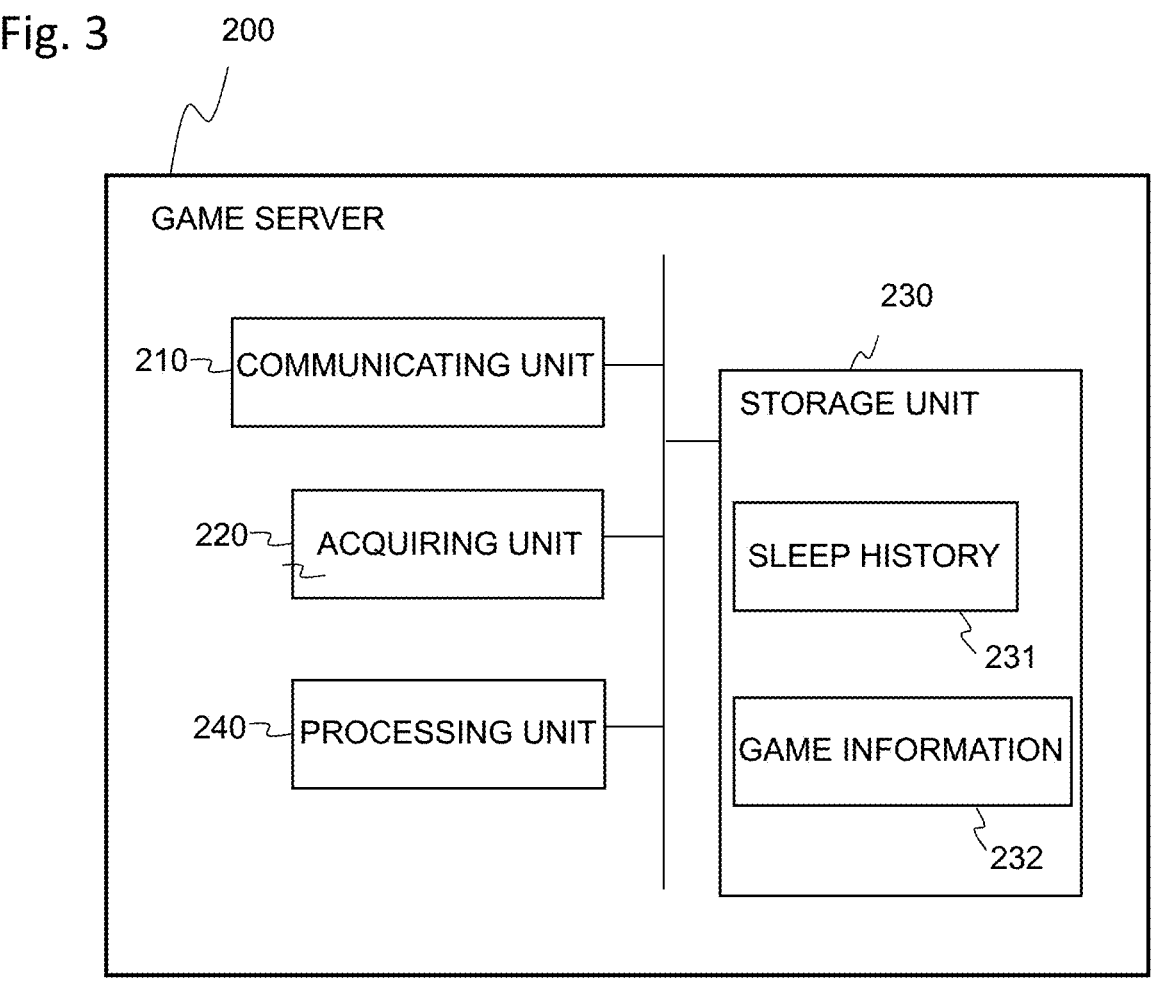
FIG. 3 is a functional block diagram showing an example of a functional configuration of a game server 200.

FIG. 3 is a functional block diagram showing an example of a functional configuration of the game server 200. Alternatively, the game server 200 according to the present embodiment may be configured by omitting a part of components (respective units) shown in FIG. 3.

The game server 200 includes a communicating unit 210, an acquiring unit 220, a storage unit 230, and a processing unit 240.

The communicating unit 210 performs various kinds of control for communicating with the user terminal 100 via the network NW and a function thereof can be realized by hardware such as various kinds of processors or a communication ASIC or by a program or the like.

The acquiring unit 220 acquires sleep data having been received by the communicating unit 210 from the user terminal 100 and sends the sleep data to the storage unit 230.

The storage unit 230 is a storage apparatus for storing a program and various kinds of data that cause a computer to function. The storage unit 230 includes a sleep history 231 and game information 232.

The sleep history 231 functions as a sleep history storage unit and accumulates sleep data of the user acquired by the acquiring unit 220 or, in other words, a sleep pattern indicating a bedtime and a wake-up time of the user. The game information 232 stores information related to the breeding game of the virtual life form. Alternatively, the storage unit 230 may include a temporary storage area or a storage. In addition, the storage unit 230 may be configured to store sensing data having been received by the communicating unit 210 from the user terminal 100.

The processing unit 240 executes various kinds of information processing to be executed in the game server 200. The processing unit 240 has a CPU and a memory, and various kinds of information processing are executed by having the CPU use the memory to execute an information processing program stored in the storage unit 230. In the present embodiment, as the information processing described above, the processing unit 240 executes a processing step related to the breeding game based on a sleep pattern in the sleep history. In addition, the processing unit 240 may execute a processing step related to the breeding game based on various kinds of information having been detected by the user terminal 100. A processing result related to the breeding game is transmitted to the user terminal 100. Alternatively, the processing unit 240 may perform progress processing of the breeding game in accordance with a random number result that corresponds to acquired sleep data. Furthermore, the processing unit 240 acquires a present time and date using a system clock.

It should be noted that, in the present embodiment, a "server" is a term that means, in addition to a single information processing apparatus (in other words, a server apparatus), an entire server apparatus group (in other words, a server system) when a server is constituted by a plurality of server apparatuses. In addition, in the present embodiment, while the game server 200 will be described as an integral construction, the game server 200 may be a construction including a plurality of server apparatuses divided according to function and/or role. For example, the game server 200 may be a construction including a data server that stores sleep data acquired from the user terminal 100 and a service server that provides a game service based on the sleep data. Furthermore, when the game server 200 performs a service of providing an item as a part of the game service, the game server 200 may be a construction including a shop server that provides items and performs billing.

Figure 4:
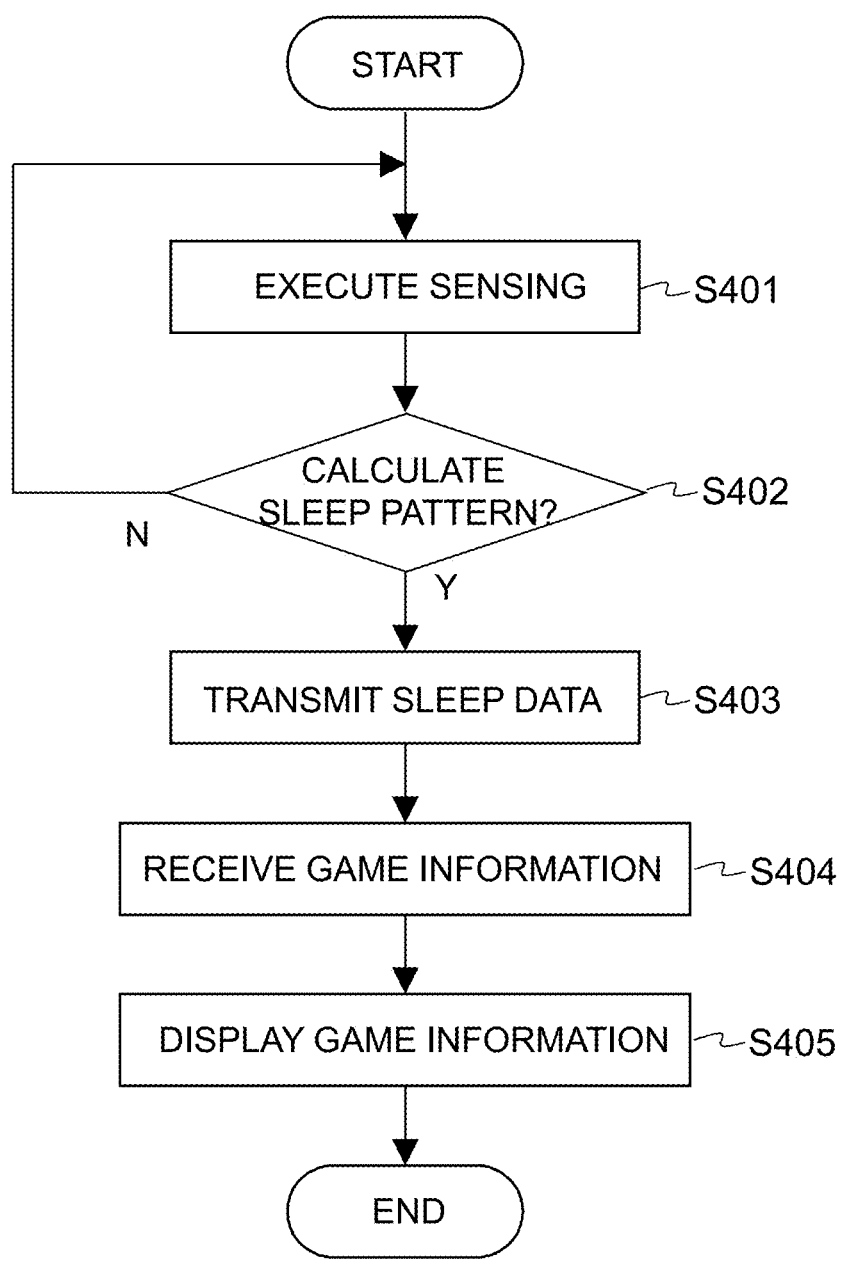
FIG. 4 is a flow chart showing an example of processing in the user terminal 100.

FIG. 4 is a flow chart showing an example of processing in the user terminal 100. An example of processing by the user terminal 100 will be described with reference to FIG. 4. The user terminal 100 may use an input operation by the user to the effect of going to bed as a trigger to start the processing. The input operation by the user to the effect of going to bed may be, for example, an operation of interrupting the breeding game or an operation of putting the virtual life form to sleep (petting the virtual life form, turning off a light in a virtual space being used by the virtual life form, or the like via the touch panel). In addition, sensing can be constantly executed by the sensor unit 150, in which case the user terminal 100 can detect that the user has gone to sleep based on sensing data (for example, a motion of the terminal or brightness or audio in the periphery of the terminal). Furthermore, the user may be prompted to go to bed by showing the virtual life form in a drowsy state or also turning the world inside the game into night as the reference bedtime (described in detail with reference to FIG. 6) approaches.

In step S401, the processing unit 160 of the user terminal 100 instructs the sensor unit 150 to execute sensing. Specifically, the sensor unit 150 senses a motion of the user terminal 100 or biological data of the user such as a heart rate. The processing unit 160 acquires sensing data from the sensor unit 150.

In step S402, based on the sensing data having been sent from the sensor unit 150, the processing unit 160 determines whether or not a sleep pattern indicating a bedtime and a wake-up time can be calculated. When the processing unit 160 determines that a sufficient amount of sensing data that enables a sleep pattern to be calculated has not been acquired (N in step S402), the processing returns to step S401. Otherwise (Y in step S402), the processing unit 160 calculates a sleep pattern and the processing is advanced to step S403.

In step S403, the processing unit 160 instructs the communicating unit 110 to transmit sleep data including the calculated sleep pattern to the game server 200.

In step S404, the communicating unit 110 receives game information having been transmitted from the game server 200 in accordance with the sleep data transmitted in step S403 and transmits the game information to the processing unit 160.

In step S405, the processing unit 160 instructs the output unit 130 to output the game information received in step S404 and ends the processing.

Figure 5:
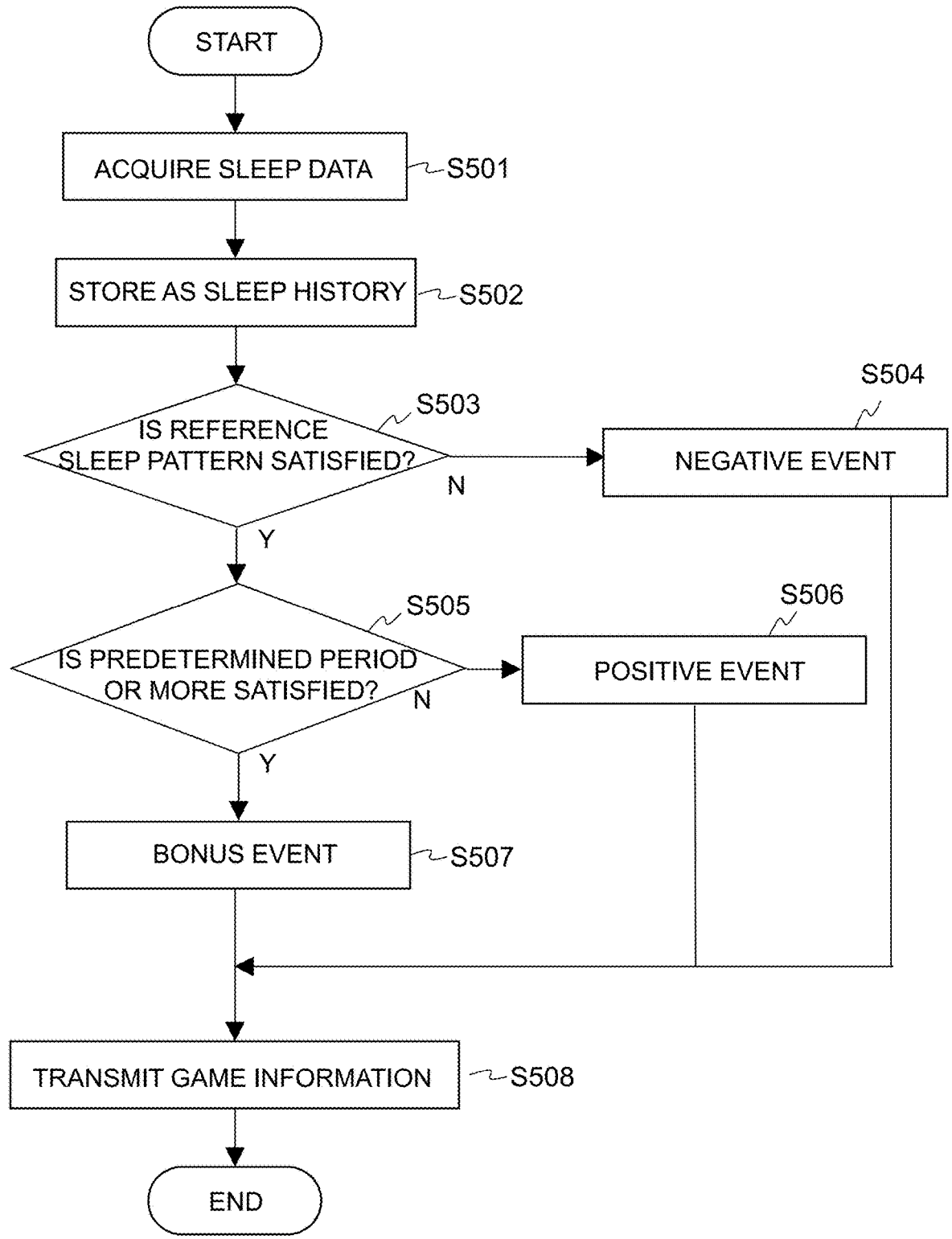
FIG. 5 is a flow chart showing processing in the game server 200.

FIG. 5 is a flow chart showing processing in the game server 200. An example of processing by the game server 200 will be described with reference to FIG. 5. In FIG. 5, the game server 200 may use a reception of sleep data from the user terminal 100 as a trigger to start the processing.

In step S501, the acquiring unit 220 of the game server 200 acquires, via the communicating unit 210, sleep data including a sleep pattern that indicates a bedtime and a wake-up time of the user having been transmitted from the user terminal 100 and sends the sleep data to the storage unit 230.

In step S502, the storage unit 230 stores the sleep data in the sleep history 231 as a sleep history.

In step S503, the processing unit 240 determines whether or not a sleep pattern based on the sleep history stored in the sleep history 231 satisfies a reference sleep pattern. The reference sleep pattern refers to a sleep pattern based on a reference bedtime and a reference wake-up time set by the user or a game developer of the breeding game or the like.

Alternatively, the processing unit 240 may recognize a regular sleep pattern of the user based on the sleep history and set the recognized sleep pattern as the reference sleep pattern. Since sleep patterns differ from one individual to the next, setting a reference sleep pattern in accordance with each person based on the sleep history enables the user to practice sleep habits that match the user's constitution without being strained.

Figure 6:
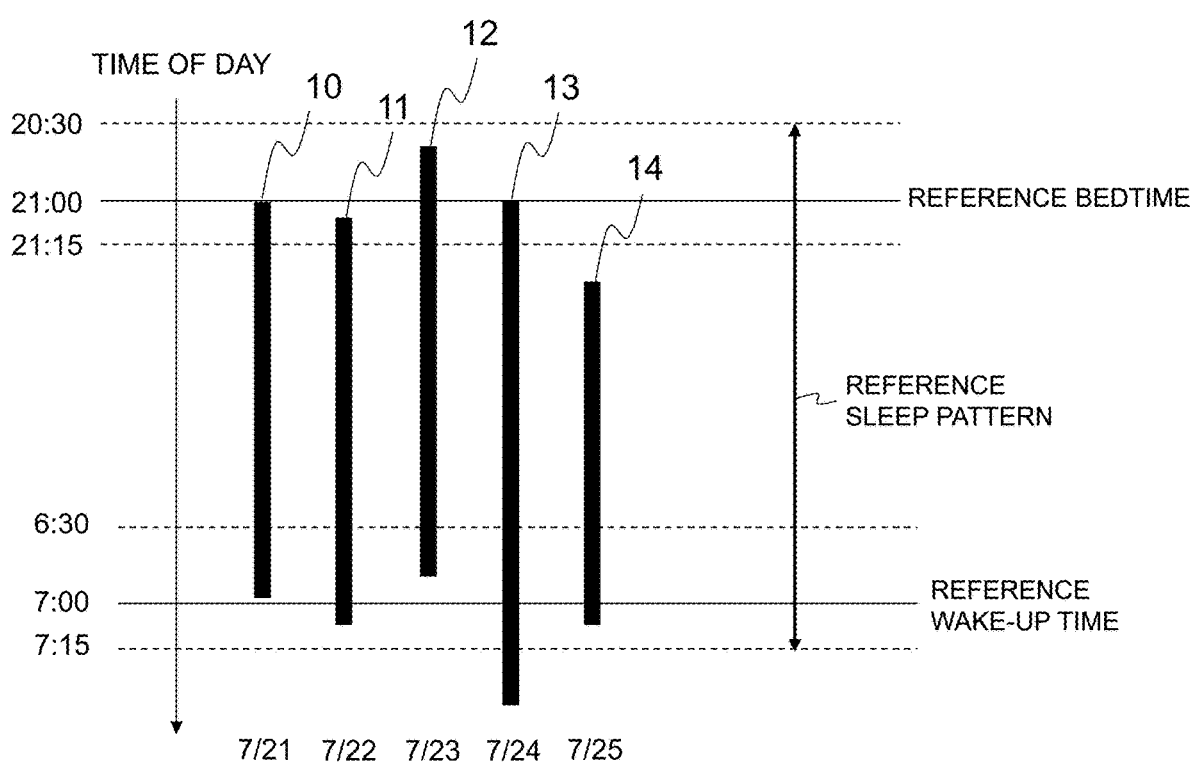
FIG. 6 is a diagram for explaining an example of determination of a reference sleep pattern.

FIG. 6 is a diagram for explaining an example of determination of the reference sleep pattern. An example of a criterion for determining whether or not a sleep pattern satisfies the reference sleep pattern will be described with reference to FIG. 6.

In FIG. 6, an ordinate represents a time of day, an abscissa represents a date, the reference bedtime is set to 21 o'clock, and the reference wake-up time is set to 7 o'clock. With sleep patterns 10 to 14, a sleep pattern indicating a bedtime and a wake-up time is represented by a line.

The reference sleep pattern is set based on the reference bedtime and the reference wake-up time (hereinafter, the reference bedtime and/or the reference wake-up time may be described as a reference time) and an allowance may be added to a time slot of the reference sleep pattern within a range in which a minimum sleep time is secured. In the example shown in FIG. 6, an allowance is added as a range from 30 minutes before the reference time to 15 minutes after the reference time. The allowance added to the reference time may differ between before and after the reference time. For example, from the perspective of promoting going to bed early and getting up early, the allowance added to the time slot before the reference time is set to be longer than after the time slot. In addition, a setting of the minimum sleep time may be changed according to the age of the user. For example, settings such as 7 hours for an adult and 10 hours for a child may be made by the user or a developer of the game.

In the sleep patterns 10 to 12, the bedtime is included in the reference bedtime (time slot) and the wake-up time is also included in the reference wake-up time (time slot).

Therefore, the processing unit 240 determines that the sleep patterns 10 to 12 satisfy the reference sleep pattern.

On the other hand, in the sleep pattern 13, while the bedtime is 21 o'clock and satisfies the reference bedtime, the wake-up time is after 7:15 and does not satisfy the reference wake-up time. Therefore, the processing unit 240 determines that the sleep pattern 13 does not satisfy the reference sleep pattern.

In the sleep pattern 14, while the wake-up time is between 7 o'clock and 7:15 and satisfies the reference wake-up time, the bedtime is after 21:15 and does not satisfy the reference bedtime. Therefore, the processing unit 240 determines that the sleep pattern 14 does not satisfy the reference sleep pattern.

As described above, the processing unit 240 determines whether or not a sleep pattern satisfies the reference sleep pattern.

When the sleep data acquired from the user terminal 100 suggests that, conceivably, a problem has occurred in sensing by the user terminal 100 such as sleep time being fragmented or sleep time not being detected, the processing unit 240 may assume a sleep pattern based on an amount of daytime activity of the user such as the number of steps taken by the user. For example, when the processing unit 240 determines that a problem has occurred in sensing by the user terminal 100, the processing unit 240 acquires sensing data related to the amount of activity of the user from the user terminal 100. In addition, when the amount of activity of the user on a given day is an average amount of activity of the user, an average sleep pattern that is calculated based on a previous sleep history of the user is assumed. Accordingly, even when a problem occurs in the detection of sleep data, implementing such a relief measure prevents the breeding game from progressing in an disadvantageous manner to the user.

Returning now to FIG. 5, in step S503, the processing unit 240 determines whether or not the sleep pattern based on the sleep history stored in the sleep history 231 satisfies the reference sleep pattern or, in other words, whether or not the sleep pattern of the sleep data having been acquired from the user terminal 100 satisfies the reference sleep pattern, and when it is determined that the sleep pattern does not satisfy the reference sleep pattern (N in step S503), in step S504, the processing unit 240 executes a processing step of generating a negative event in the breeding game and causes a processing result to be stored in the game information 232 of the storage unit 230. Details of events in the breeding game will be provided later.

On the other hand, when it is determined that the sleep pattern satisfies the reference sleep pattern (Y in step S503), in step S505, the processing unit 240 determines whether or not the sleep pattern continuously satisfies the reference sleep pattern for a predetermined period or more based on the sleep history. When it is determined that the sleep pattern based on the sleep history does not satisfy the reference sleep pattern for a predetermined period or more (N in step S505), in step S506, the processing unit 240 executes a processing step of generating a positive event in the breeding game and causes a processing result to be stored in the game information 232 of the storage unit 230. When it is determined that the sleep pattern based on the sleep history satisfies the reference sleep pattern for a predetermined period or more (Y in step S505), in step S507, the processing unit 240 executes a processing step of generating a bonus event that differs from the positive event in the breeding game and causes a processing result to be stored in the game information 232 of the storage unit 230.

As the predetermined period, for example, the user may set an arbitrary number of days such as three days or a week. By having the user set the predetermined period for generating a bonus event by himself/herself, the predetermined period can be used as a goal to strive for in terms of continuing good sleep habits, and generating a bonus event can impart a sense of achievement to the user.

In addition, the developer of the game may set the predetermined period as an internal parameter of the game. The user can stay motivated toward practicing good sleep habits while waiting expectantly for a bonus event to occur and, by generating the bonus event, a sense of surprise as well as a sense of satisfaction can be imparted to the user.

In step S508, the processing unit 240 transmits processing in the game as game information to the user terminal 100 via the communicating unit 210 and ends the processing.

The processing unit 240 may generate a mini-game in addition to generating the respective events described above. Causing the user to play the mini-game prevents the user from falling back to sleep. The mini-game requires the user to perform some kind of task. For example, as an aspect of the mini-game, a game that requires the user to perform an operation that involves actually moving his/her body is preferable such as a mini-game for arousing, playing with, or petting the virtual life form by shaking the terminal itself or tapping or swiping the display or a mini-game that enables the user to capture the virtual life form by standing up and taking a predetermined number of steps. Accordingly, an effect of reliably waking up the user can be expected.

Furthermore, the mini-game may be configured to be played within a predetermined time from a time of occurrence of each event. Providing an incentive such as giving points (to be described later) when the mini-game is completed can be used as motivation to not fall back to sleep.

Figure 7:
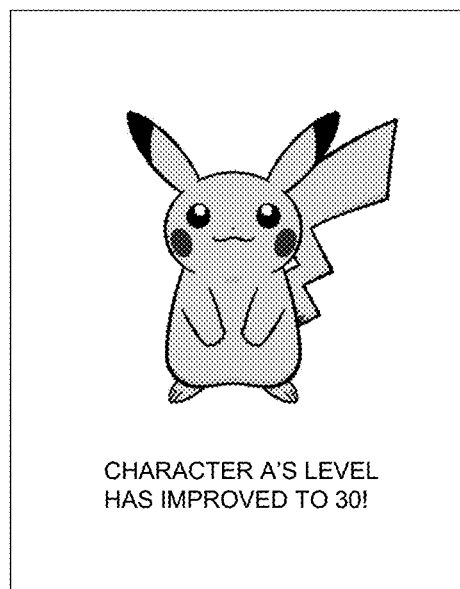
FIG. 7 is a diagram showing an example of a positive event.
Figure 8:
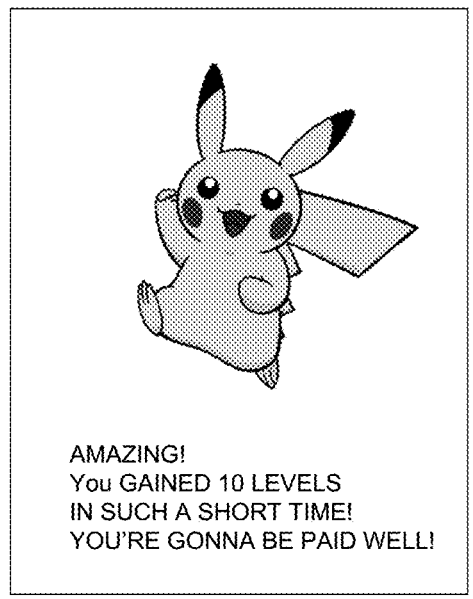
FIG. 8 is a diagram showing an example of a bonus event.
Figure 9:
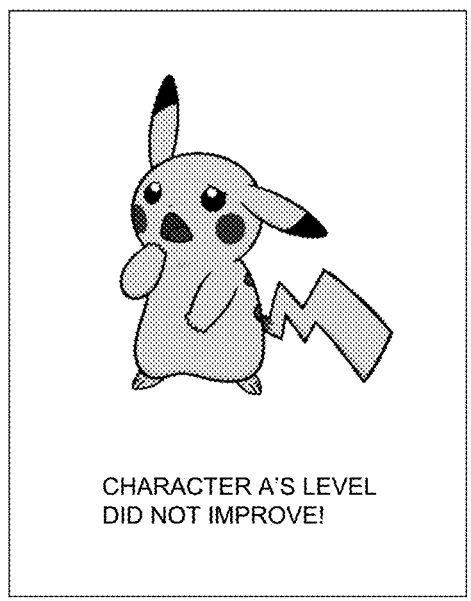
FIG. 9 is a diagram showing an example of a negative event.

FIGS. 7 to 9 are diagrams for explaining examples of events in the breeding game. Examples of a positive event, a bonus event, and a negative event in the breeding game will now be described with reference to FIGS. 7 to 9. The processing unit 240 may be configured to change contents of each event in accordance with a random number result that corresponds to acquired sleep data.

FIG. 7 is a diagram showing an example of a positive event. The positive event is an event for causing the breeding game to progress in an advantageous manner which occurs when the sleep pattern of the user satisfies the reference sleep pattern. For example, the positive event is one or more of an event that enables the virtual life form to grow, an event for adding points related to the virtual life form, and an event for giving items or privileges in the breeding game.

Examples of enabling the virtual life form to grow include, but are not limited to, making the virtual life form appear larger, making the virtual life form appear stronger, making the virtual life form more beautiful or handsome, causing the virtual life form to change from a child to an adult, causing the virtual life form to evolve, and causing the virtual life form to mature internally.

In addition, the points may be experience points of the virtual life form or in-game currency for purchasing items in the game. Based on a value of the points, a level of the virtual life form may be determined or various virtual life forms may be introduced. The positive event can provide the user with an incentive toward maintaining the reference sleep pattern.

In FIG. 7, a character A that is a virtual life form acquires experience points (which correspond to points) and improves its level (which corresponds to growing) in accordance with the sleep pattern of the user satisfying the reference sleep pattern. In other words, the character A grows when the sleep pattern of the user satisfies the reference sleep pattern. Accordingly, by practicing good sleep habits, the user can cause the breeding game to progress while enjoying the growing process of the character A.

FIG. 8 is a diagram showing an example of a bonus event. The bonus event is an event for causing the breeding game to progress in a particularly advantageous manner which occurs when the sleep pattern based on the sleep history satisfies the reference sleep pattern for a predetermined period or more. Examples of the bonus event include, but are not limited to, an event for facilitating the growth of the virtual life form, an event for adding points related to the virtual life form as a bonus, and an event for giving items or privileges that cause the breeding game to progress in an advantageous manner. For example, another aspect of the bonus event is an event in which the character leaves a new virtual life form with the user for the user to grow. By growing the virtual life form on the character's behalf, the user can receive a message of gratitude from the character or be awarded points or the like.

In addition, the user may be notified of an occurrence of the bonus event in advance. This can be used as motivation to continuously stick to the reference sleep pattern. Expectations of the user toward an occurrence of the bonus event can be built up by notifying the user of, for example, an introduction of a new virtual life form, addition of points, or the like on the following Sunday. The bonus event can provide the user with an incentive toward maintaining the reference sleep pattern for a predetermined period or more.

In FIG. 8, in accordance with the sleep pattern of the user satisfying the reference sleep pattern for a predetermined period or more, the virtual life form acquires experience points in an amount equal to or greater than an amount acquired by a positive event and improves its level significantly. In addition, an item (a reward) that causes the breeding game to progress in an advantageous manner is awarded. The item is endowed with a special effect such as making the level of the virtual life form more easily improved or causing other virtual life forms to appear when the item is used to put the virtual life form to sleep.

FIG. 9 is a diagram showing an example of a negative event. The negative event is an event for causing the breeding game to progress in a disadvantageous manner which occurs when the sleep pattern of the user does not satisfy the reference sleep pattern. Examples of the negative event include, but are not limited to, stopping the growth of the virtual life form, causing the virtual life form to devolve, making the virtual life form weaker, and subtracting points related to the virtual life form. For example, as another aspect of the negative event, when (a length of) the sleep time of the user is shorter than a time determined based on the reference time, a rate of breeding may be made slower by making the virtual life form appear to be drowsy during the day or the like. In other words, when the user is deprived of sleep, growth of the virtual life form is inhibited as long as the user stays awake. The negative event can cause the user to maintain the reference sleep pattern and become conscious of practicing good sleep habits.

In FIG. 9, the character A that is a virtual life form is unable to acquire experience points and its level has not been improved in accordance with the sleep pattern of the user not satisfying the reference sleep pattern. In addition, the character A may be endowed with a special effect causing the character A to appear out of sorts by consuming (subtracting) points indicating a degree of health or a vitality level related to the character A.

As described above, processing related to the breeding game is executed as shown in, for example, FIGS. 7 to 9 based on a sleep pattern.

In the breeding game, a degree of difficulty may be set to putting the virtual life form to sleep. For example, at the start of the breeding game, a virtual life form of which a degree of difficulty of putting the virtual life form to sleep is low may be bred and a level of the virtual life form may be set so as to be readily improvable. Accordingly, the breeding game can be readily enjoyed and can lead to a well-regulated sleep pattern.

In addition, the degree of difficulty of putting the virtual life form to sleep may be increased as the breeding game progresses. In other words, since it becomes difficult to improve the level of the virtual life form, the user can be made conscious of causing an occurrence of a positive event or a bonus event for improving the level and the user can be prompted to continue a well-regulated sleep pattern.

Furthermore, game characteristics may be enhanced by having the user breed a plurality of virtual life forms and setting a degree of difficulty of putting one of the virtual life forms to sleep so as to affect a degree of difficulty of putting another virtual life form to sleep. For example, when the user is awake past the reference bedtime, a virtual life form of which a degree of difficulty of putting the virtual life form to sleep is high is introduced and the virtual life form that is being bred is made less susceptible to falling asleep (in other words, a degree of difficulty of putting the virtual life form to sleep is increased). Since the introduction of a virtual life form of which a degree of difficulty of putting the virtual life form to sleep is high causes the degree of difficulty of putting the virtual life form that is currently being bred to sleep to increase, the user can be made conscious toward going to bed so as not to exceed the reference bedtime. Accordingly, the user can continuously enjoy the game and, by extension, the user can be motivated to continue a well-regulated sleep pattern.

(Description of advantageous effect)

The game system according to the present embodiment executes processing steps related to a breeding game based on sleep data including a sleep pattern indicating a bedtime and a wake-up time of a user. Since a well-regulated lifestyle practiced by the user leads to breeding a virtual life form, the user can stay motivated toward practicing good sleep habits while enjoying breeding the virtual life form.

In addition, the game system according to the present embodiment generates various events in the breeding game in accordance with the sleep pattern. Generating different events enables the user to enjoy the game without becoming bored and, at the same time, an incentive towards practicing good sleep habits can be imparted to the user.

Second Embodiment

A game system according to a second embodiment further acquires a history of positional information of a user when a jet lag is detected from sleep data and, based on the history of positional information, adds mileage of an airline or the like as points with respect to a virtual life form.

Since organs inside a human body operate in a metronomic rhythm, when a long-distance movement is performed in a short period of time for travel, business purposes, or the like, the rhythm is disrupted by a time difference and causes a change in physical conditions, and may sometimes result in deteriorated physical conditions such as an inability to sleep at night. In such a case, since jet lag causes a sleep pattern to significantly deviate from the reference sleep pattern, a negative event is generated in the breeding game and takes away motivation from the user who has been practicing good sleep habits up to then. The present embodiment enables even a user having experienced a jet lag to enjoy the breeding game.

Figure 10:
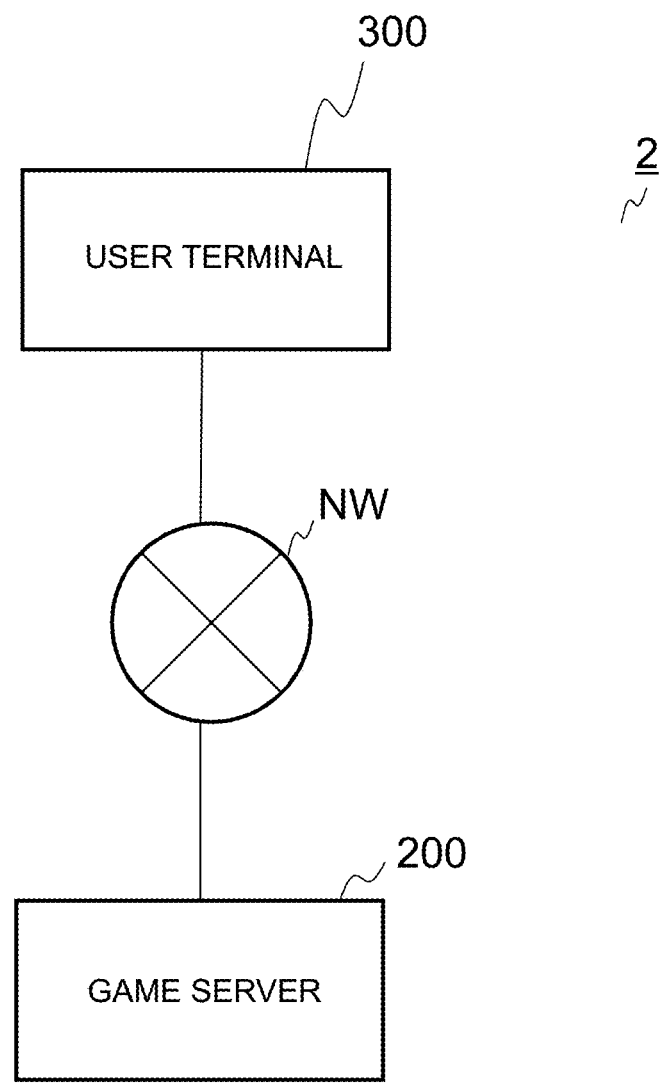
FIG. 10 is a configuration diagram of a game system 2.

FIG. 10 is a configuration diagram of a game system 2. The game system 2 according to the second embodiment includes a user terminal 300 and a game server 200 which are connected to be capable of communicating with each other via a network NW. While only one user terminal 300 is shown in FIG. 10, in the present embodiment, the game system 2 includes a plurality of user terminals 300 of which each is provided for each user.

Figure 11:
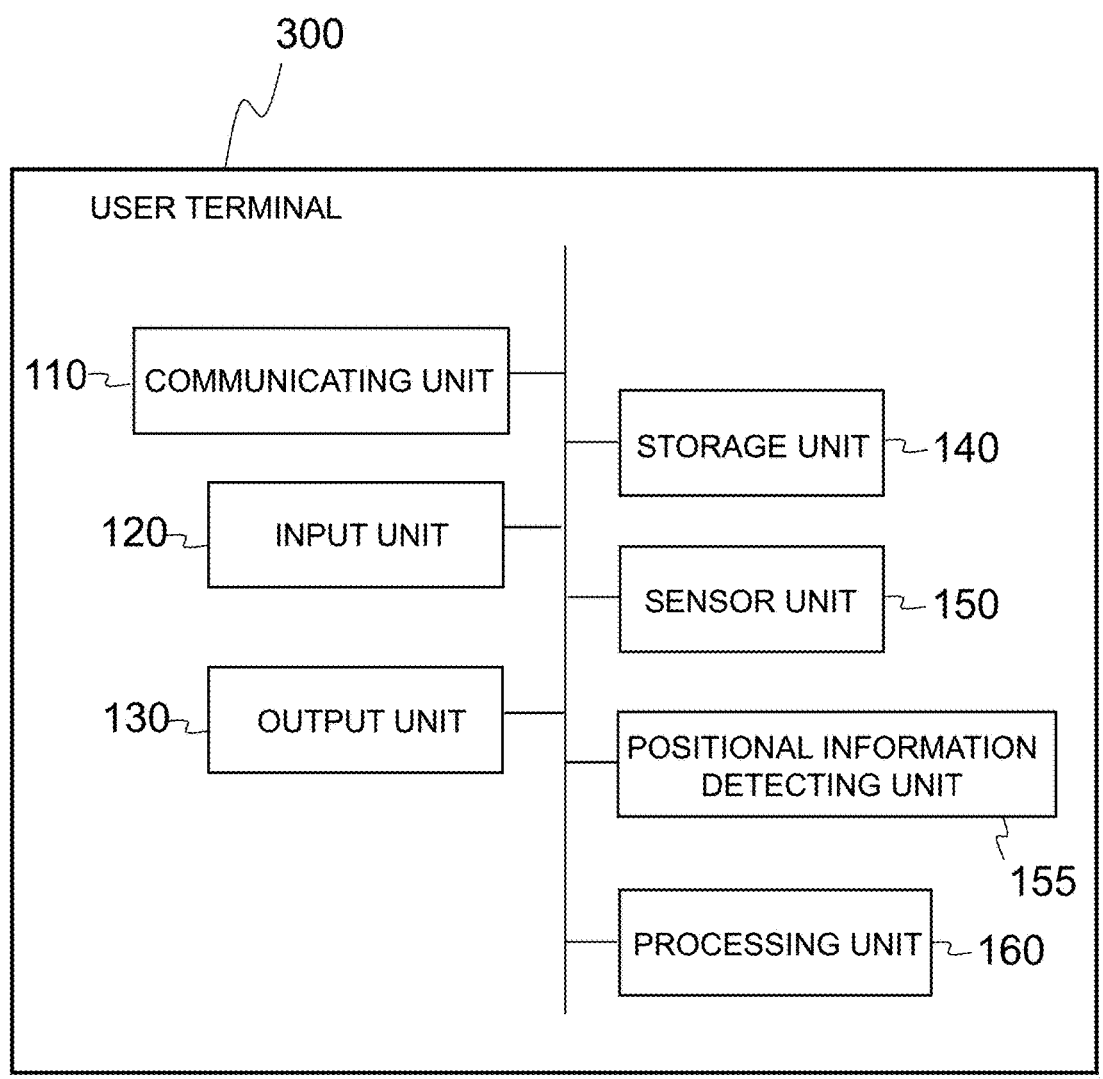
FIG. 11 is a functional block diagram showing an example of a functional configuration of a user terminal 300.

FIG. 11 is a functional block diagram showing an example of a functional configuration of the user terminal 300. The user terminal 300 according to the second embodiment differs in configuration from the user terminal 100 according to the first embodiment in that the user terminal 300 includes a positional information detecting unit 155. Alternatively, the user terminal 300 according to the present embodiment may be configured by omitting a part of components (respective units) shown in FIG. 11.

The positional information detecting unit 155 detects a position of the user terminal 300. In the present embodiment, the positional information detecting unit 155 detects a position using a GNSS (Global Navigation Satellite System). For example, the positional information detecting unit 155 is a GPS (Global Positioning System) sensor (for example, a GPS module). It should be noted that a position detection method that is employed by the positional information detecting unit 155 is arbitrary and, for example, the positional information detecting unit 155 may detect a position using a beacon. In addition, for example, when the user terminal 300 includes a function comparable to a contactless IC card that is used at station ticketing gates, stores, and the like (or when the user terminal 300 includes a function of reading a history of a contactless IC card), the positional information detecting unit 155 records a position where the user terminal 300 had been used together with information to the effect that a transaction of a train fare or the like was made at a station. The positional information detecting unit 155 may detect this information and acquire the information as positional information. In addition, for example, when the user terminal 300 communicates with a specific access point, the positional information detecting unit 155 may detect acquirable positional information from the access point. Furthermore, the positional information detecting unit 155 may detect a position at which the user terminal 300 is estimated to be present based on identification information (such as an IP address) upon the user terminal 300 connecting to the Internet.

The positional information detecting unit 155 transmits the detected positional information to the game server 200 via the communicating unit 110. The positional information may be accumulated for a predetermined period in the user terminal 300 and transmitted to the game server 200 as a history of positional information or positional information may be transmitted every time positional information is detected. The game server 200 stores the positional information acquired from the user terminal 300 as a history of positional information.

The processing unit 240 of the game server 200 detects a jet lag based on a sleep pattern of sleep data transmitted from the user terminal 300 which is stored in the sleep history 231.

Figure 12:
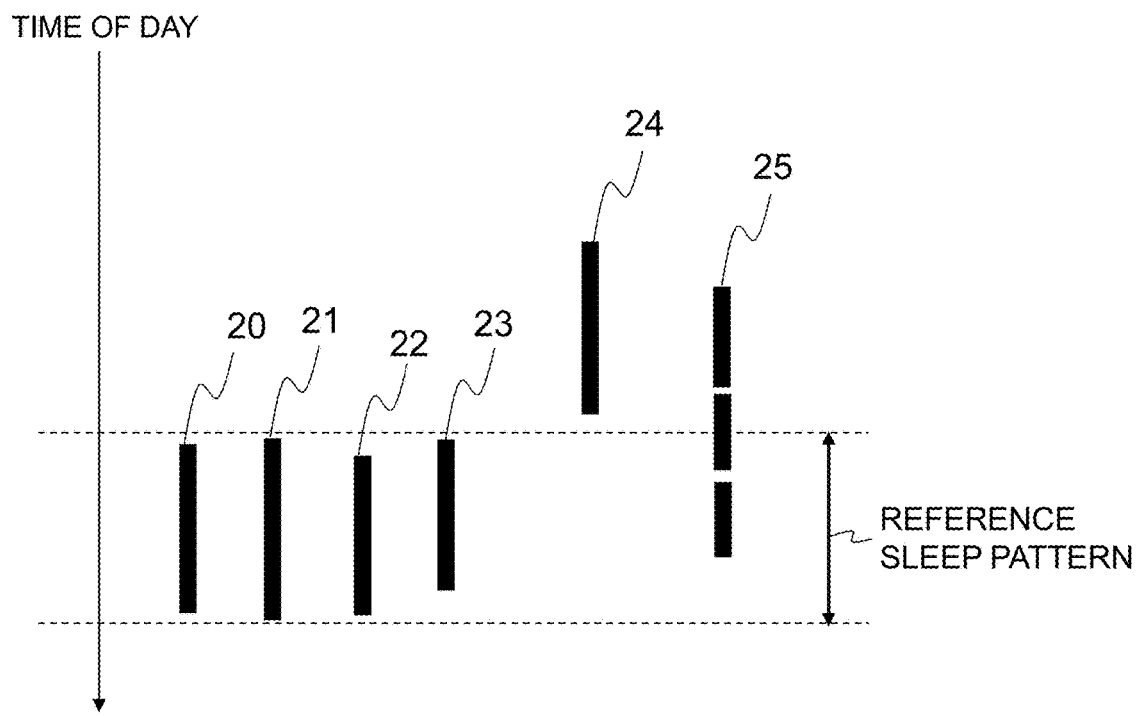
FIG. 12 is a diagram for explaining a detection example of a jet lag.

FIG. 12 is a diagram for explaining a detection example of a jet lag. FIG. 12 shows sleep patterns 20 to 25. The sleep patterns 20 to 23 are sleep patterns that satisfy the reference sleep pattern. On the other hand, in the sleep pattern 24, both a bedtime and a wake-up time deviate significantly from the reference time. In addition, in the sleep pattern 25, the reference sleep pattern is not satisfied and falling asleep and waking up are repeated in a discontinuous manner.

When a sleep pattern that clearly differs from the sleep pattern of a prior sleep history is detected as described above, the processing unit 240 may determine that a jet lag has occurred. In addition, a sleep pattern to be a criterion for determining a jet lag may be stored in advance, an input to the effect that the user has performed a long-distance movement including a time difference may be accepted from the user, or an occurrence of a jet lag may be determined when a long-distance movement is detected from a history of positional information having been transmitted from the user terminal 300.

Upon detecting a jet lag, the processing unit 240 of the game server 200 calculates a travel distance of the user terminal 300 based on a history of positional information acquired from the user terminal 300. In addition, the processing unit 240 adds a mileage in accordance with the travel distance (miles) as points with respect to a virtual life form in the breeding game. Mileage refers to a point program implemented by airlines. A mile refers to a unit of points in the point program. By incorporating a concept of mileage into the breeding game, even when a negative event is generated due to a disruption in sleep habits caused by a jet lag, the user can cause the breeding game to progress in an advantageous manner using the added points and, at the same time, motivation for returning to good sleep habits can be provided.

Alternatively, in order to promptly improve the jet lag of the user, the processing unit 240 may add points in accordance with time after the occurrence of the jet lag and until the user returns to a well-regulated sleep pattern. Accordingly, the user can be further motivated to return to good sleep habits.

Third Embodiment

In a game system according to a third embodiment, sleep data includes information related to quality of sleep of a user. By causing the breeding game to progress based on sleep data including information related to the quality of sleep, the user's consciousness toward practicing better sleep habits can be raised.

In this case, information related to the quality of sleep refers to a time of each sleep stage in a sleep cycle or a ratio of each sleep stage to sleep time. Examples of information related to the quality of sleep include a time or ratio of "awakening", "light sleep", "deep sleep", and "REM sleep" which are the respective sleep stages of a sleep cycle.

In the third embodiment, a user terminal calculates information related to sleep of the user from biological data of the user having been detected by a sensor unit. The information related to sleep of the user may be calculated by adopting a known function for analyzing sleep of an existing multi-functional device that functions as the user terminal.

Figure 13:
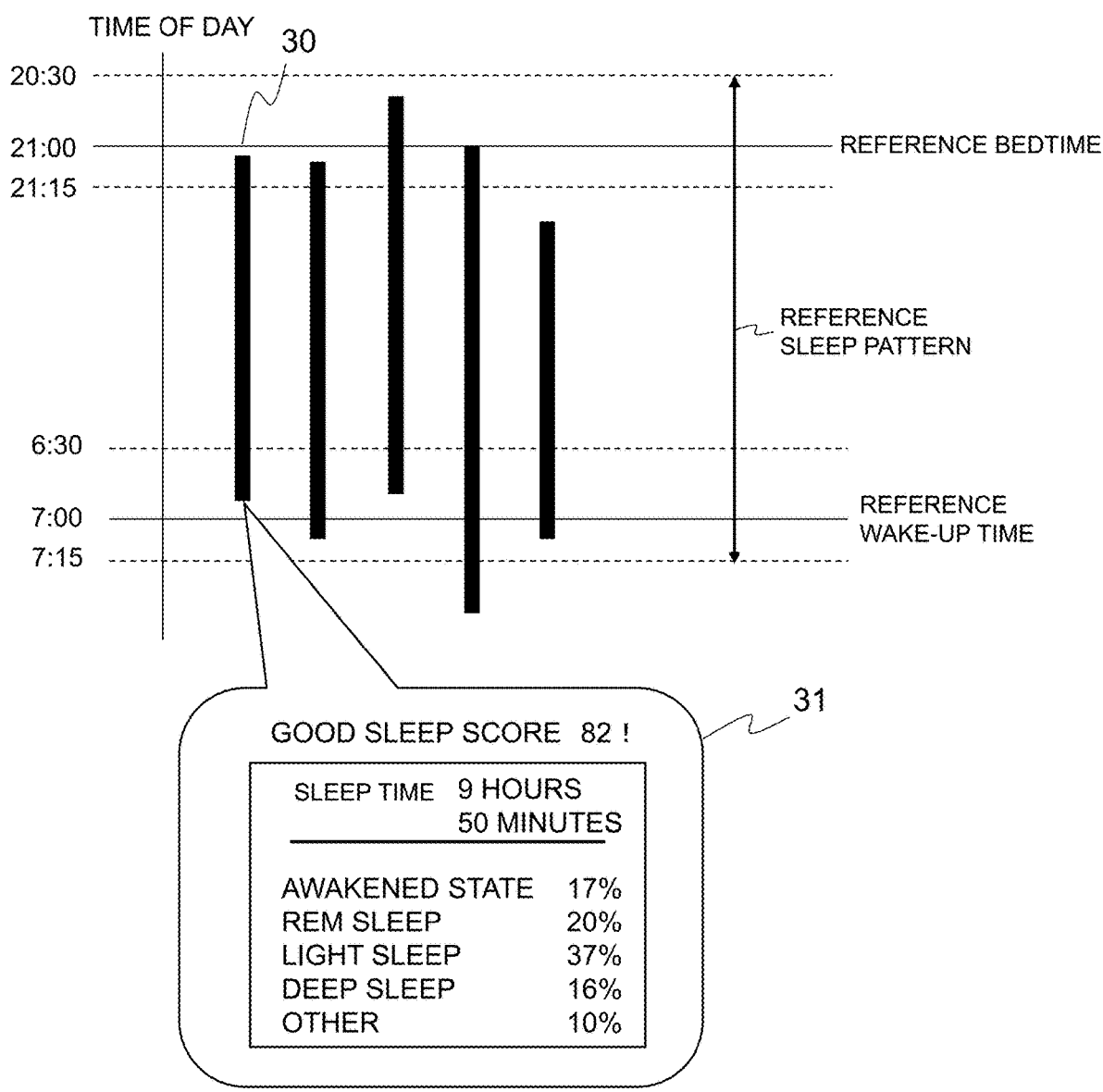
FIG. 13 is a diagram for explaining an example of information related to quality of sleep.

FIG. 13 is a diagram for explaining an example of information related to the quality of sleep. In FIG. 13, a sleep result 31 is displayed with respect to a sleep pattern 30. For example, the user can confirm the sleep result 31 by selecting the sleep pattern 30.

The sleep result 31 includes a sleep time calculated from the sleep pattern 30 and a ratio of each sleep stage to the sleep time. ("Other" refers to, for example, a time including a state where a sleep stage is indeterminate, an awakened state despite being in bed, and the like).

In addition, the sleep result 31 may include a good sleep score that is an index indicating whether sleep is good or not based on the sleep stage. The good sleep score may be calculated by weighting each sleep stage and using an arbitrary algorithm created by a game developer. Alternatively, the good sleep score may be calculated in accordance with an amount of activity, diet, a location, humidity, an operation time of a user terminal, an operation time slot of the user terminal, and the like. For example, when a location of a highly-acclaimed hotel (such as a five-star hotel) is detected as the positional information of the user terminal, the good sleep score may be added on the assumption that good sleep is likely to be provided. In addition, for example, the good sleep score may be reduced when the user terminal is operated after the reference bedtime. The good sleep score enables the user to recognize, in one glance, whether or not the user had a good night's sleep and motivates the user to practice good sleep habits.

The game server may adopt the good sleep score as a parameter that affects the progress of the breeding game. Examples include, but are not limited to, causing the virtual life form to change, generating an event, and adding points or privileges.

Adopting the good sleep score as a parameter that affects the progress of the breeding game enables the user's consciousness toward practicing good sleep habits to be raised and, at the same time, provides the user with further motivation toward becoming actively involved in the breeding game.

Fourth Embodiment

A user terminal according to a fourth embodiment executes a game program stored in a storage unit to cause a user to play a breeding game of a virtual life form based on sleep data of the user. A configuration may be adopted in which the game program stored in the user terminal can be updated via a network or a storage medium.

Figure 14:
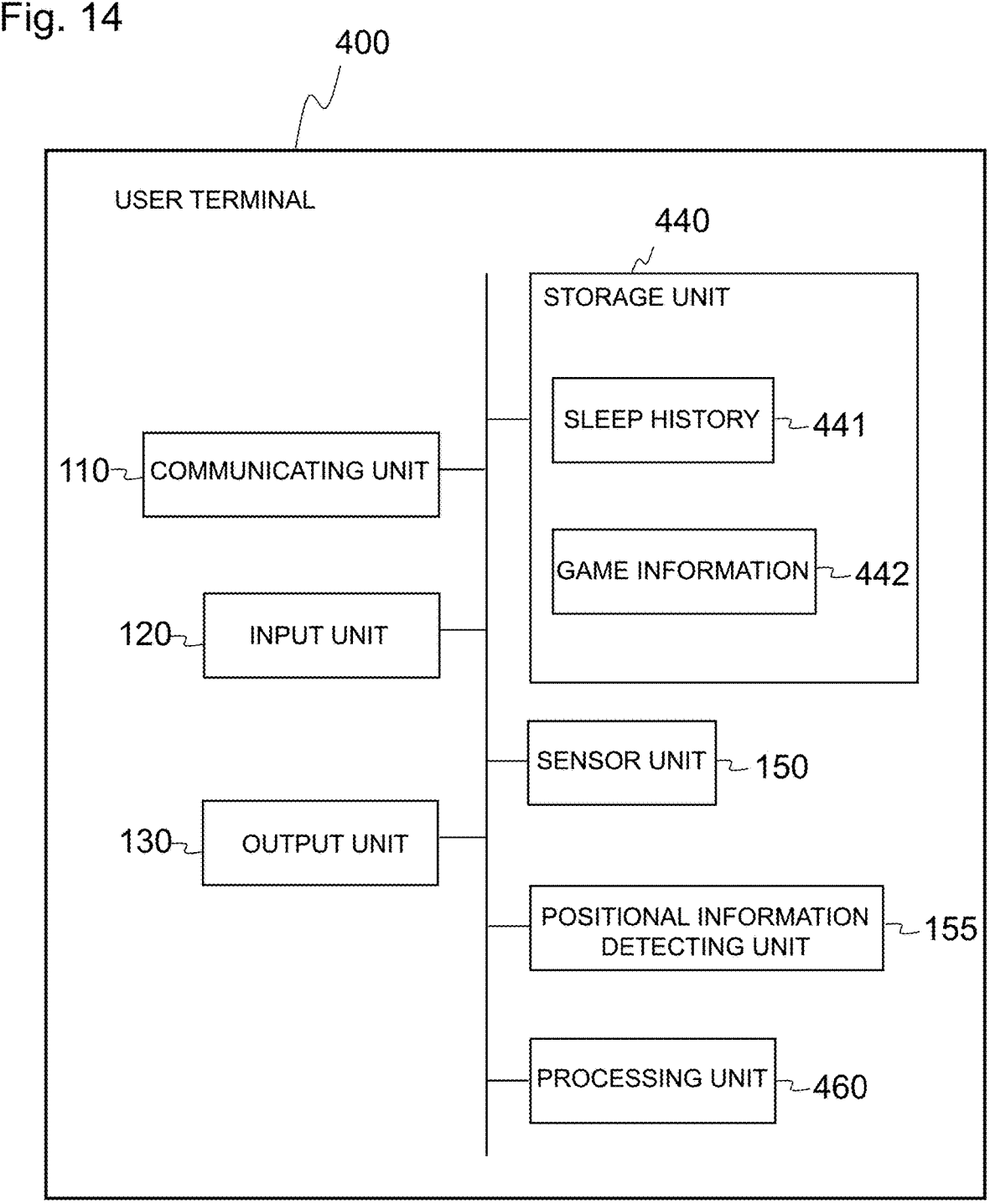
FIG. 14 is a functional block diagram showing an example of a functional configuration of a user terminal 400.

FIG. 14 is a functional block diagram showing an example of a functional configuration of a user terminal 400. The user terminal 400 according to the fourth embodiment corresponds to an information processing terminal and differs in configuration from the user terminal 300 according to the second embodiment (refer to FIG. 11) in that the user terminal 400 includes a storage unit 440 and a processing unit 460. However, since other components denoted by same reference signs have common functions, repetitive descriptions thereof will be omitted. Alternatively, the user terminal 400 according to the present embodiment may be configured by omitting a part of components (respective units) shown in FIG. 14.

The storage unit 440 is a storage apparatus for storing a program and various kinds of data that cause a computer to function. The storage unit 440 includes a sleep history 441 and game information 442.

The sleep history 441 functions as a sleep history storage unit and accumulates sleep data of the user calculated by the processing unit 460 to be described later or, in other words, a sleep pattern indicating a bedtime and a wake-up time of the user. The game information 442 stores information related to the breeding game of the virtual life form. Alternatively, the storage unit 440 may include a temporary storage area or a storage. In addition, the storage unit 440 may be configured to store sensing data having been detected by the sensor unit 150.

The processing unit 460 executes various kinds of information processing to be executed in the user terminal 400. The processing unit 460 has a CPU and a memory, and various kinds of information processing are executed by having the CPU use the memory to execute an information processing program stored in the storage unit 440. In the present embodiment, as the information processing described above, the processing unit 460 executes a processing step of calculating a sleep pattern and a processing step related to the breeding game based on a sleep pattern in the sleep history. In addition, the processing unit 460 may execute a processing step related to the breeding game based on various kinds of information having been detected by the sensor unit 150. A processing result related to the breeding game is output to the output unit 130. Alternatively, the processing unit 460 may perform progress processing of the breeding game in accordance with a random number result that corresponds to the calculated sleep data. Furthermore, the processing unit 460 acquires a present time and date using a system clock.

As described above, the user terminal according to the present embodiment can provide a breeding game of a virtual life form based on sleep data of a user. Accordingly, the user can enjoy the breeding game even in an environment in which the user is unable to connect to a game server via a network.

The embodiments described above can be implemented in various other forms, and various omissions, replacements, and modifications can be made without departing from the gist of the invention. It is to be understood that such embodiments and modifications thereof are included in the scope and gist of the invention and are also included in the invention as set forth in the claims and the equivalents thereof.

In addition, as a program (software means) that can be executed by a computer, the methods described in the embodiments presented above can be stored in a storage medium such as magnetic disk (a flexible disk, a hard disk, or the like), an optical disc (a CD-ROM, a DVD, an MO, or the like), or a semiconductor memory (a ROM, a RAM, a flash memory, or the like) and can be distributed by being transmitted from a communication medium. The program stored in the medium includes a configuration program that constructs, inside a computer, software means (also including tables and data structures in addition to an executable program) to be executed by the computer. The computer that realizes the present server reads the program stored in the storage medium and, in some cases, constructs the software means using the configuration program, and executes the processing steps described earlier by having the software means control operations. It should be noted that the term "storage medium" as used in the present specification is not limited to those intended to be distributed and also includes storage media such as a magnetic disk and a semiconductor memory provided inside the computer or in a device being connected via a network.

What is claimed is:

1. An information processing apparatus that manages progress of a game using sleep information executed on a user terminal, the information processing apparatus comprising:

circuitry configured to
  acquire sleep information including information on a ratio of each sleep stage in a sleep cycle relative to a total sleep time, wherein the sleep cycle includes a plurality of sleep stages,
  control an appearance of a character in the game according to the information on the ratio of each sleep stage to the total sleep time, and
  in response to a determination that a problem has occurred acquiring the sleep information, determine a sleep pattern based on an amount of daytime activity of the user, wherein the sleep pattern is based on a previous sleep history corresponding to the amount of daytime activity of the user.

2. The information processing apparatus according to claim 1, wherein the circuitry is further configured to
  control a growth of the character in the game according to the information on the ratio of each sleep stage.

3. The information processing apparatus according to claim 1, wherein the circuitry is further configured to
  determine a privilege that affects the progression of the game according to the information on the ratio of each sleep stage.

4. The information processing apparatus according to claim 1, wherein the circuitry is further configured to
  determine contents of a character performance in the game according to the information on the ratio of each sleep stage.

5. The information processing apparatus according to claim 1, wherein the user terminal is equipped with a touch panel.

6. The information processing apparatus according to claim 5, wherein the one sleep time is calculated from the user's sleeping time and waking time.

7. The information processing apparatus according to claim 6, wherein the sleeping time and the waking time are set based on the user's operation of the touch panel.

8. The information processing apparatus of claim 1, wherein in response to the total sleep time being less than an amount of time set as a reference sleep pattern, the circuitry is further configured to change an appearance of the character for a same amount of time as a difference between the total sleep time and the amount of time set as the reference sleep pattern.

9. The information processing apparatus of claim 1, wherein the amount of daytime activity of the user is a number of steps taken by the user.

10. A non-transitory computer-readable storage medium storing computer-readable instructions thereon which, when executed by a computer, cause the computer to perform a method, the method comprising:
  acquiring sleep information including information on a ratio of each sleep stage in a sleep cycle relative to a total sleep time, wherein the sleep cycle includes a plurality of sleep stages;
  controlling an appearance of a character in the game according to the information on the ratio of each sleep stage to the total sleep time; and
  in response to a determination that a problem has occurred acquiring the sleep information, determining a sleep pattern based on an amount of daytime activity of the user, wherein the sleep pattern is based on a previous sleep history corresponding to the amount of daytime activity of the user.

11. The non-transitory computer-readable storage medium of claim 10, further comprising:
  controlling a growth of the character in the game according to the information on the ratio of each sleep stage.

12. The non-transitory computer-readable storage medium of claim 10, further comprising:
  determining a privilege that affects the progression of the game according to the information on the ratio of each sleep stage.

13. The non-transitory computer-readable storage medium of claim 10, further comprising:
  determining contents of a character performance in the game according to the information on the ratio of each sleep stage.

14. The non-transitory computer-readable storage medium of claim 10, wherein the user terminal is equipped with a touch panel.

15. The non-transitory computer-readable storage medium of claim 14, wherein the one sleep time is calculated from the user's sleeping time and waking time.

16. The non-transitory computer-readable storage medium of claim 15, wherein the sleeping time and the waking time are set based on the user's operation of the touch panel.

17. A method of managing progress of a breeding game of a virtual life form to be executed on a user terminal, the method comprising:
  acquiring sleep data including information related to a quality of sleep of the user, wherein the information related to a quality of sleep of the user includes information on each sleep stage of a plurality of sleep stages in a sleep cycle;
  setting a parameter that affects progress of the breeding game to the user in accordance with a ratio of each sleep stage in the sleep cycle relative to a total sleep time; and in response to a determination that a problem has occurred acquiring the sleep information, determining a sleep pattern based on an amount of daytime activity of the user, wherein the sleep pattern is based on a previous sleep history corresponding to the amount of daytime activity of the user.

18. A game system in which a user terminal and a game server that manages progress of a breeding game of a virtual life form to be executed on the user terminal are connected to each other via a network, wherein
  the game server includes circuitry configured to:
  acquire sleep data including information related to a quality of sleep of the user, wherein the information related to a quality of sleep of the user includes information on each sleep stage of a plurality of sleep stages in a sleep cycle,
  set a parameter that affects progress of the breeding game to the user in accordance with a ratio of each sleep stage in the sleep cycle relative to a total sleep time; and
  in response to a determination that a problem has occurred acquiring the sleep information, determine a sleep pattern based on an amount of daytime activity of the user, wherein the sleep pattern is based on a previous sleep history corresponding to the amount of daytime activity of the user.

19. An information processing terminal that executes a breeding game of a virtual life form to be executed on a user terminal, the information processing terminal comprising:
  circuitry configured to
    acquire sleep data including information related to a quality of sleep of the user, wherein the information related to a quality of sleep of the user includes information on each sleep stage of a plurality of sleep stages in a sleep cycle, set a parameter that affects progress of the breeding game to the user in accordance with a ratio of each sleep stage in the sleep cycle relative to a total sleep time; and in response to a determination that a problem has occurred acquiring the sleep information, determine a sleep pattern based on an amount of daytime activity of the user, wherein the sleep pattern is based on a previous sleep history corresponding to the amount of daytime activity of the user.

20. The information processing terminal of claim 19, wherein the plurality of sleep stages in the sleep cycle includes awakening, light sleep, deep sleep, and REM sleep.

* * * * *